United States Patent
Patterson

(10) Patent No.: US 6,521,265 B1
(45) Date of Patent: *Feb. 18, 2003

(54) METHOD FOR APPLYING A BLOOD CLOTTING AGENT

(75) Inventor: James A. Patterson, Sarasota, FL (US)

(73) Assignee: Biolife, L.L.C., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/592,344

(22) Filed: Jun. 13, 2000

Related U.S. Application Data

(63) Continuation-in-part of application No. 09/500,902, filed on Feb. 9, 2000, now Pat. No. 6,187,347.

(51) Int. Cl.⁷ .................. A61K 33/26; A61K 9/00; A61K 31/14; A61K 31/28; A61K 31/74; A61K 33/00; A61K 47/00

(52) U.S. Cl. .............. 424/646; 424/405; 424/406; 424/407; 424/409; 424/484; 424/486; 424/489; 424/501; 424/78.1; 424/613; 424/617; 424/618; 424/620; 424/621; 424/629; 424/630; 424/638; 424/639; 424/641; 424/642; 424/644; 424/647; 424/648; 424/649; 424/650; 424/652; 424/653; 424/654; 424/655; 424/682; 424/719; 424/722; 514/492; 514/493; 514/495; 514/496; 514/498; 514/499; 514/500; 514/501; 514/502; 514/503; 514/504; 514/505; 514/642; 514/769; 514/772; 514/772.3; 514/834; 514/974

(58) Field of Search .................. 424/400, 443, 424/445, 446, 447, 600, 613, 615, 616, 617–618, 620, 621, 629, 630, 638, 639, 641, 642, 644, 646, 647, 648, 649, 650, 652, 653, 654, 655, 661, 667, 673, 682, 703, 709, 713, 719, 722, 405, 406, 407, 409, 484, 486, 489, 501, 78.1; 514/642, 834, 492, 493, 495, 496, 498, 499, 500, 501, 502, 503, 504, 505, 769, 772, 772.3, 974

(56) References Cited

U.S. PATENT DOCUMENTS 2,491,416 A * 12/1949 Olson et al. ................ 424/617
6,187,347 B1 * 2/2001 Patterson et al. ........... 424/646

OTHER PUBLICATIONS

Remington's Pharmaceutical Sciences (17th Ed. 1985), p. 1580.*

* cited by examiner

*Primary Examiner*—Jose' G. Dees
*Assistant Examiner*—Frank Choi
(74) *Attorney, Agent, or Firm*—Charles J. Prescott

(57) ABSTRACT

A method of arresting the flow of blood and other protein containing body fluids flowing from an open wound and for promoting wound healing. In the method, a substantially anhydrous compound of a salt ferrate is provided for a unique use which, when hydrated after mixing with a victim's own blood or other aqueous media, produces $Fe^{+++}$ thereby promoting clotting when applied in a paste form to the wound for a time sufficient to arrest substantial further blood and other body fluid flow from the wound. The compound is formed of a ferrate (VI) salt taken from the group consisting of H, Li, Na, K, Rb, Cs and Fr. However, to decrease or eliminate stinging sensation, the compound may be formed having a ferrate (VI) salt taken from the group consisting of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi, Al, As, $NH_4$ and $N(C_4H_9)_4$. The preferred composition also includes a cation exchange material such as sulfonated ion exchange resin as an admixture which, when combined with the ferrate (VI) salt, will hydrate in the presence of blood or other aqueous media to produce $Fe^{+++}$, thereby promoting clotting of the blood and body fluid and to produce oxygen. The cation exchange material produces a scab or protective coating over the wound for protection and enhanced healing. Oxygen produced during the reaction substantially reduces the level of bacteria, virus and fungus at the wound. The compound must be stored dry unmixed together and mixed into a paste with the victim's blood or other aqueous media just prior to its application to the wound.

19 Claims, No Drawings

METHOD FOR APPLYING A BLOOD CLOTTING AGENT

This is a continuation-in-part of Ser. No. 09/500,902 filed Feb. 9, 2000, now U.S. Pat. No. 6,187,347.

BACKGROUND OF THE INVENTION

1. Scope of Invention

This invention relates generally to topically applied agents for promoting blood clotting to arrest blood flow from an open wound, and more particularly to a method of applying an anhydrous composition which may be mixed just prior to its application directly over an open bleeding wound or a wound from which body fluid is flowing to accelerate flowing blood and body fluid clotting and enhance healing.

2. Prior Art

In addition to conventional bandages, adhesive means, compresses and the like which are applied with pressure directly against a bleeding open wound, considerable effort has been directed toward the development of chemical agents in various forms which accelerate or enhance the coagulation of blood flowing from an open wound to arrest blood flow. Many of these agents are in the "clotting chain", i.e., fibrinogen, thrombin, Factor VIII and the like. Others are based upon the use of collagens. Edwardson, in U.S. Pat. Nos. 5,763,411, 5,804,428, and 5,962,026, for example, teaches the use of fibrin in conjunction with a solid support in the '411 patent, and as an enzyme free sealant in the '428 patent, and as a solid composition substantially free of catalytic enzymes.

Three U.S. Patents invented by Martin, U.S. Pat. Nos. 5,692,302, 5,874,479 and 5,981,606, are generally directed to the use of pyruvate in combination with fatty acids and an oxidant as a therapeutic wound healing composition.

Stilwell, in U.S. Pat. No. 5,484,913 teaches the use of calcium-modified oxidized cellulose to promote faster hemostasis. In U.S. Pat. No. 5,474,782, Winter, et al. teaches a wound healing composition or its salt present in a pharmaceutically acceptable carrier, the preferred embodiment being a salt of sodium. Winter provides a wound dressing with a taspine compound for promoting healing rather than clotting.

In U.S. Pat. No. 2,163,588, Cornish teaches a wound pad having very fine fibers carrying a viscous agent and a septic for arresting and clotting blood flow. Eberl, et al., in U.S. Pat. No. 2,688,586, teaches an improved hemostatic surgical dressing with alginic acid as a clotting agent. Masci, et al. in U.S. Pat. Nos. 2,772,999 and 2,773,000 also teaches hemostatic surgical dressing including a pad and free acid cellulose glycolic acid.

A patent for another hemostatic wound dressing is taught by Shelley in U.S. Pat. No. 3,206,361 having an active agent in the form of methylaminoacetocatechol hydrochloride. Likewise, Anderson, in U.S. Pat. No. 3,328,259, another wound dressing containing a film of cellulose glycolic acid ether is provided as the hemostatic agent.

The hemostatic agent taught by Sugitachi, et al. as disclosed in U.S. Pat. No. 4,265,233 is blood coagulation Factor VIII plus either fibrin or thrombin. A ready-to-use bandage is taught by Altshuler in U.S. Pat. No. 4,363,319 which also contains thrombin as an active agent, the bandage all of which is contained within a sealed package.

Invented by Lindner, et al., a wound pad which is impregnated with tissue-compatible protein such as collagen and lyophilized Factor XIII, thrombin and fibrinogen, are taught in U.S. Pat. No. 4,600,574. The use of collagen as a hemostatic agent within a pad that has been freeze dried is taught by Sawyer in U.S. Pat. No. 4,606,910.

In U.S. Pat. No. 4,616,644, Saferstein, et al. teaches the use of an adhesive bandage with high molecular weight polyethylene oxide applied to the surface of the perforated plastic film wound release cover of the bandage to arrest blood flow from minor cuts. Yet another hemostatic agent including a carrier in the shape of a flake or fiber having thrombin and Factor XIII affixed thereto is taught by Sakamoto in U.S. Pat. No. 4,655,211. The use of an ultra-pure, clean thrombin solution as a hemostatic agent is taught in U.S. Pat. No. 5,525,498 invented by Boctor. Two recent patents invented by Pruss, et al., U.S. Pat. Nos. 5,643,596 and 5,645,849 both teach the use of hemostatic dressings which incorporate thrombin and epsilon aminocaproic acid (EACA) and calcium chloride on gelatin.

An absorbable spun cotton-like topical hemostat is taught by Shimuzu, et al. in U.S. Pat. No. 5,679,372. This disclosure is directed to an absorbable dressing made of acetocollagen fibers which are innately adhesive to a bleeding surface. In a patent to Bell, et al, U.S. Pat. No. 5,800,372, a dressing made of microfibrillar collagen and a superabsorbant polymer provides both blood absorption and clotting inducement.

One embodiment of the present method utilizes an improved ion exchange resin, preferably in the form of a styrene divinylbenzene copolymer which has been sulfonated. The collective teaching of making this prior art resin is to be found in an earlier patent to co-inventor, Patterson, U.S. Pat. No. 4,291,980 which was based at least in part on the production of spherical beads comprised of copolymer styrene and divinylbenzene as taught in U.S. Pat. Nos. 2,366,007 and 3,463,320. This collective teaching is incorporated herein by reference. An improvement better adapting this resin to the present invention is in the form of substantially reduced cross-linking down to about 0.25%.

Another primary aspect of the present method incorporates a salt ferrate, preferably potassium ferrate ($2K_2FeO_4$). The teaching of a process for producing alkaline metal ferrates is taught by another co-inventor, Thompson, in U.S. Pat. No. 4,545,974. This teaching is also incorporated herein by reference.

It is submitted that the above-referenced prior art, either taken individually or collectively in any combination thereof fail to teach a method of preparing a flowing blood or body fluid clotting agent just prior to its application which includes an admixture of a salt ferrate which produces a trivalent $Fe^{+++}$ ion which reacts with the blood to accelerate coagulation and clotting of the blood. Moreover, the utilization of an insoluble cation exchange material, e.g. a sulfonated ion exchange resin, in combination with the salt ferrate, additionally produces a protective covering over the wound and also produces oxygen which acts as an antibacterial, antiviral and antifungal agent. Further, the presence of selected salts neutralize hydroxide radicals as clotting occurs so as to eliminate any substantial stinging sensation.

BRIEF SUMMARY OF THE INVENTION

This invention is directed to a method of arresting the flow of blood and other body fluid from an open wound and for promoting wound healing. In the method, a substantially anhydrous compound of a salt ferrate is provided for unique use which is hydrated just prior to its use by mixing it into a paste using the victim's own blood or other aqueous media. $Fe^{+++}$ is produced thereby promoting clotting of the blood and other body fluids when applied to the open wound for a time sufficient to effect clotting of the blood or body fluid to arrest substantial further flow from the wound. The anhydrous compound is formed of a monovalent, divalent, or trivalent salt ferrate ($M_2FeO_4$, $M_2'FeO_4$ or $M_2''FeO_4$) taken from the cationic group consisting of H, Li, Na, K, Rb, Cs and Fr. However, to decrease or eliminate stinging sensation, the compound may be formed having a salt taken from the cationic group consisting of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi, Al, As, $NH_4$, and $N(C_4H_9)_4$. The preferred composition includes the substantially anhydrous salt ferrate compound and a sulfonated ion exchange resin as an admixture which will hydrate in the presence of blood or other aqueous selected media to produce $Fe^{+++}$, thereby promoting clotting of the blood and oxygen. The resin produces a scab or protective coating over the wound for protection and enhanced healing. Oxygen produced during the reaction substantially reduces the level of bacteria, virus and fungus at the wound.

It is therefore an object of this invention to provide a method of utilizing a salt ferrate as a blood clotting agent for arresting blood flow from an open surface wound.

It is another object of this invention to provide a method of arresting blood and body fluid flow utilizing a salt ferrate composition which is substantially sting-free when applied onto an open wound.

It is still another object of this invention to provide an anhydrous composition utilizing a salt ferrate combined with an insoluble cation exchange material and mixed with an aqueous media just prior to use for arresting blood flow from an open skin wound.

Still another object of this invention is to provide a method for preparing a localized rapid forming protective coating or covering just prior to its use that has antibacterial, antifungal and antiviral properties.

In accordance with these and other objects which will become apparent hereinafter, the instant invention will now be described.

DETAILED DESCRIPTION OF THE INVENTION

Mechanism of Blood Coagulation

The following is offered as a brief explanation of one possible mechanism which would explain the effectiveness of the present invention as described herebelow in full detail.

The plasma of circulating blood normally remains a liquid with it's colloidal protein in the solid state. After albumin, the second most abundant protein in mammalian blood is a long, large molecule called fibrinogen. A series of enzymatic reactions take place during the clotting of blood. An inactive plasma enzyme (prothrombin) is converted into an active enzyme (thrombin) which, in turn, removes two pairs of amino acid groups from each fibrinogen molecule, converting into a molecule called fibrin monomer. Fibrin monomer then links together to form a polymer, which is the visible clot. The reactions can be summarized as follows:

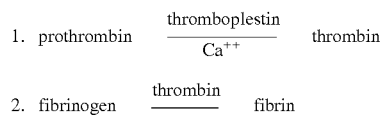

It is known that the decomposition of potassium ferrate produces the finest particles of iron oxide ($Fe_2O_3$) available.

(See U.S. Pat. No. 4,545,974). Upon addition to water, $K_2FeO_4$ becomes $Fe^{+++}$ in the form of FeOOH, which upon drying, yields $Fe_2O_3$. The FeOOH (or $Fe_2O_3H_2O$) is a solid in suspension and this ultra-fine material seems to be an ideal irritant for platelet membranes, thereby releasing the prothroplastin that is needed to initialize clotting. It is possible that they may tend to rupture the platelets themselves, thereby causing a massive release of clotting factors as does the rough surface of a wound achieve the same end.

It is possible that the $Fe^{+++}$ ion itself may aid in coagulation of blood. Trivalent ions, by lowering the zeta potential of a particle in solution, allow the particles (platelets) to clump more easily. Platelets are small disks of cytoplasm found in the blood of mammals. After a wound is received they begin to clump and stick around the wound area, causing the clumping and sticking of another cytoplasmic component, the thrombocyte. During this clumping process, certain phospholipids from the membrane of the platelets contribute to the overall clotting process, combined with the inactive plasma enzyme, Factor XII. Mechanical abrasion of the platelets is important in freeing the phospholipid component from the platelets.

Range of Useful Salt Ferrates

Initially, applicants have found that the utilization of potassium ferrate, again likely based upon the above-recited theory, effectively accomplishes the accelerated clotting of blood flowing from an open wound. The apparent chemical ferrate reaction with water found in blood is as follows:

$$2K_2FeO_4 \rightarrow 4\ K^+OH^- + Fe_2O_3 + 3/_2O_2\uparrow + 2H_2O \qquad 3.$$

$$KOH + Fe_2O_3 \rightarrow Fe(OH)_3\downarrow + K^+ + OH^- \qquad 4.$$

$$Fe(OH)_3 \rightarrow Fe^{+++} + 3(OH)^- \qquad 5.$$

One of the important results is the production of the trivalent $Fe^{+++}$ ion which appears to be the beneficial clotting agent provided in this aspect of this invention. Moreover, it has been determined that the present invention acts on all body fluids containing protein, such as that which flows from an open skin blister or burn.

A broadening of this aspect of the inventive compound would be to substitute the potassium salt with others which possess the same cation properties as does the potassium cation. Those salt elements which will substitute for the potassium cation are shown in Tables I and II herebelow.

TABLE I

| | |
|---|---|
| H | Hydrogen |
| Li | Lithium |
| Na | Sodium |
| K | Potassium |
| Rb | Rubidium |
| Cs | Cesium |
| Fr | Francium |

TABLE II

| | | | | | |
|---|---|---|---|---|---|
| Be | Beryllium | Mg | Magnesium | Ca | Calcium |
| Sr | Strontium | Ba | Barium | Ra | Radium |
| Ti | Titanium | V | Vanadium | Cr | Chromium |
| Mn | Manganese | Fe | Iron | Co | Cobalt |
| Ni | Nickel | Cu | Copper | Zn | Zinc |
| Ga | Gallium | Ge | Geranium | Zr | Zirconium |
| Nb | Niobium | Mo | Molybdenum | Tc | Technetium |
| Ru | Ruthenium | Rh | Rhodium | Pd | Palladium |
| Ag | Silver | Cd | Cadmium | In | Indium |

TABLE II-continued

| Sn | Tin | Hf | Hafnium | Ta | Tantalum |
|---|---|---|---|---|---|
| W | Tungsten | Re | Rhenium | Os | Osmium |
| Ir | Iridium | Pt | Platinum | Au | Gold |
| Hg | Mercury | Tl | Thallium | Pb | Lead |
| Bi | Bismuth | Al | Aluminum | As | Arsenic |
| NH$_4$ | Cation | N(C$_4$H$_9$)$_4$ | Cation | | |

In addition to the above salts in the cation form, all zeolites, sulfonated coal, and natural reoccurring membranes such as protein membranes will also act in compound form with ferrate to release the trivalent $Fe^{+++}$ ion to effect blood and body fluid coagulation.

Eliminating Stinging Effect

In utilizing the $K_2 Fe O_4$ as above described to arrest blood flow from a bleeding wound, equation 3 shows the presence of hydroxide (OH)$^-$ radicals which are produced. The hydroxide (OH)$^-$ radicals remain present in equation 5 and cause stinging at the wound site. Moreover, all of the cation salts of Table I produce the same result, i.e. stinging caused by the presence of the hydroxide ion.

All of the cation salts listed in Table II, however, produce a slightly altered chemical reaction which neutralizes all of the hydroxide ions produced. For example, using a calcium cation salt to replace the potassium cation causes the following chemical reaction with water in blood:

$$2CaFeO_4 \rightarrow 2Ca(OH_2)_2 + Fe_2O_3 + 3/_2O_2 \uparrow H_2O \qquad 6.$$

As can be observed from Equation 6, no hydroxide ions are produced. Rather, all are neutralized and combined with calcium as shown in the equation.

As provided by the above compounds, a method of arresting blood and body fluid flow from an open skin wound is provided. An effective amount of any of the above salt ferrates, and preferably potassium ferrate in powder form, is applied directly onto the wound to interact with flowing blood or body fluid to accelerate its clotting.

Salt Ferrate Combined with Resin

Although the above methodology and utilization of a salt ferrate greatly enhances blood clotting, the wound nonetheless remains opened and generally unprotected unless the salt ferrate is combined with a carrier such as a BAND-AID, bandage, cotton member and the like which has been impregnated or coated with a dry powder taken from of one of the above chosen salt ferrate compositions.

By the addition of an ion exchange resin R with the salt ferrate, an additional benefit of scabbing or depositing of a substance produced by the reaction with water in the blood is accomplished over the open wound. Details of the composition and method of producing the preferred ion exchange resin R in the form of styrene divinylbenzene are disclosed in the previously referenced patents and are herein incorporated by reference. As described in formulas herebelow, the resin R may be shown in its chemical form or generally designated by the symbol "R" for simplicity. The ion exchange resin R is sulfonated as is shown in chemical terms in each chemical equation herebelow.

An acid form of the sulfonated ion exchange resin R in acid form is shown symbolically as follows:

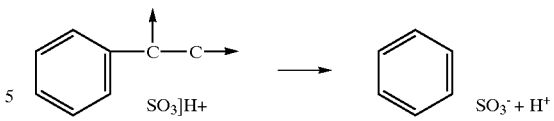

When the preferred hydrogen form of this sulfonated ion exchange resin R is in the presence of the salt ferrate and water within blood, the following reaction serves to neutralize the hydroxyl ions produced in equation 3 above.

7.

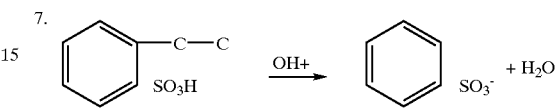

In addition to neutralizing hydroxyl ions by the presence of even trace amounts of the resin R to decrease or totally eliminate the stinging effect, excess trivalent $Fe^{+++}$ ions interact with the resin as follows:

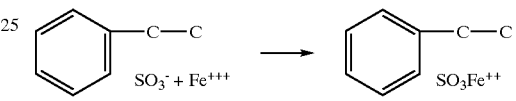

Thus, excess trivalent $Fe^{+++}$ charged ion cross links with the clotting blood in accordance with the following equation:

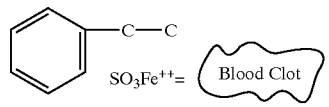

The amino acid in the blood protein are shown to interact with the resin:

The $K_2 Fe O_4$ should be hygroscopic, small particles approximately 50 to 100 mesh size for best surface area. The ion exchange resin R is preferably in an acid form with some substitute Ca calcium ions as shown in equations 6 to 9. The cross linking of the resin R should be below 4.0 and as low as 0.25% and hygroscopic. The weight ratio should favor the dry ion exchange resin R by at least 4 to 1 of dry salt ferrate. The ion exchange resin R is preferably a cation exchange resin.

In another embodiment, a small amount of divalent calcium Ca++ may be added as an additional anticoagulant. Heparin—EDTA (Ethylene Dismine Tetracacitic Acid) potassium oxalate are anticoagulants and are ionic in action on the divalent Calcium $Ca^{++}$ and trivalent ion $Fe^{+++}$ to prevent clotting. By supplying excess of these ions, i.e. $Fe^{+++}$, clotting can be induced. Also, in addition to the hydrogen form of the resin R—a given ratio of the calcium salt

 $SO_3+1$   $SO_3)_2 = CA^{++}$ can supply excess of this ion to further induce blood clotting. The ferrate in contact with the blood-water on the skin forms $O_2$ which is a strong disinfectant to the cut.

SUMMARY OF BENEFITS

By combining even a trace amount of the above-described sulfonated resin $RSO_3$ as an admixture with potassium ferrate ($K_2FeO_4$), the following benefits are derived:

1. The trivalent $Fe^{+++}+3\ RSO_3$ produces blood clotting and blood flow stoppage;
2. Oxygen produced by the reaction serves as an antibacterial, antiviral and antifungal agent;
3. The blood clotting with resin R produces a scab that acts as a protective coating for the wound;
4. Even trace amounts of resin R in this admixture neutralizes hydroxyl ions to prevent stinging.

EXAMPLE 1

Anhydrous Powder Preparation

A ferrate-ion exchange resin admixture (moisture free) was prepared for direct application to a bleeding injury as follows:

| | |
|---|---|
| 200 μ ion exchange resin in acid form (dry) | 0.79 g |
| 50 ms $K_2FeO_4$ (dry) | 0.23 g |
| Total | 1.02 g |

The cation exchange resin R was prepared in the washed hydrogen form, and then dried at 110° for 24 hours and powdered in grinder to about 100 mesh.

This composition was then applied directly to a fresh bleeding finger wound produced by a skin lancet having a penetration of 1.6–2.2 mm. The subject was 77 years old, skin condition non-flexible. Wound blood flow was at a rate of 0.206 g/30 seconds or 0.0412 g per minute to 0.0606 g per minute.

When a single penetration of the skin was made and blood flow started at 0.0412 to 0.0605 g per minute, application of 5 sec. of the above resin-ferrate composition directly to the wound dropped blood to zero as determined with a blot pickup of 0.0020 g within 1.0 minute. The resin-ferrate applied was on the order of 0.0175–0.0170 grams, forming a hard protecting sterilized coating over the penetration injury by the time that blood flow from the wound was stopped.

Dosage Economy

Pretreatment Blood Flow . . . 0.0305 g blood/30 sec. (0.0605 g/min)

After treatment Blood Flow . . . 0.0010 g blood/30 sec. (0.0028 g/min

Dosage . . . 0.0174 g of anhydrous ferrate and resin admixture was used to treat wound.

At this dosage, a 30 g quantity of the composition will provide approximately 1724 separate treatments.

Method of Preparation

Just Prior to Use

The above-described anhydrous compound is preferably in the form of a combination of potassium ferrate ($K_2FeO_4$) and the acid form of low cross-linked ion exchange resin particles. Both of the materials are in powder form and are stored together in an anhydrous form (no water). They have been previously applied directly to body fluids, i.e. blood, in the dry form (powder). Using this technique, this dry compound is difficult for control as to location of application and stability on a wound.

Certain chemical reactions slow down the blood clotting action and the production of beneficial $O_2$. By controlling the neutralization of potassium hydroxide (KOH) by the acid resin, the mixing time and application time can be controlled. An aqueous media is used to mix the $K_2FeO_4$ and $RSO_3H$. Thereafter, the mixture is spread on the wound to clot the blood and stop the bleeding. Mix time and spreading time total is about five minutes working time. The amount of aqueous media is just sufficient to form a spreadable paste when combined with the ferrate (VI) salt and resin. The lower the percentage of cross-linking of the resin, and the more resin used, the greater the amount of aqueous media needed.

The aqueous media that have been shown to provide the beneficial results of the present invention are:

(1) whole blood (from wound) and body fluids;
(2) deionized water;
(3) sodium chloride (ionic, aqueous);
(4) dissolved gelatin (i.e. 2% (aqueous);
(5) carboxyl methacel (aqueous);
(6) carbohydrate solution, i.e. sugar.

The following media controlling factors have been identified as being useful in the present method:

(1) ionic aqueous additive;
(2) viscosity;
(3) osmotic pH control (between pH 2 and 10) of the aqueous media;
(4) heat (5° C.–30° C.).

EXAMPLE 2

Compound ingredients:

0.1673 grams of anhydrous cation exchange resin $RSO_3H$ [0.5% X-L]

0.0215 g. of (KT10) $K_2FeO_4$ 1.020 g. of 2% gelatin (aqueous)

Mix the resin and the $K_2FeO_4$. Then add the gelatin and mix. Within five (5) minutes, spread this paste-like mixture on the bleeding wound. The resin ferrate applied in this form controls bleeding.

EXAMPLE 3

Compound ingredients:

0.1400 gm $RSO_3$ [2.0% X-L]

0.0120 gm (KT10) $K_2FeO_4$

Mix the resin and $K_2FeO_4$ with blood from a victim's wound and then apply this paste-like mixture to the wound from which the blood was previously obtained. Cover the wound evenly with the prepared paste mixture to control the bleeding.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A method of arresting the flow of blood from a bleeding wound comprising the steps of:
   A. mixing a substantially anhydrous compound of a salt ferrate (VI) which hydrates in the presence of blood or an aqueous media to produce $Fe^{+++}$ with blood flowing from a wound of a victim or an aqueous media to form a paste;
   B. applying said paste to the wound within a short time period of about five minutes after step A for a time sufficient to effect sufficient clotting of the blood to arrest substantial further blood flow from the wound.

2. The method of claim 1, wherein:
   said compound provided in Step A is formed of a salt ferrate (VI) of H, Li, Na, K, Rb, Cs or Fr.

3. The method of claim 1, wherein:
   said compound provided in Step A is formed of a said salt ferrate (VI) of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi, Al, As, $NH_4$ or $N(C_4H_9)_4$.

4. The method of claim 1, wherein:
   said compound provided in Step A is formed of a salt ferrate (VI) of H, Li, Be, Na, Mg, K, Ca, Rb, Sr, Cs, Ba, Fr, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi, Al, As, $NH_4$ or $N(C_4H_9)_4$.

5. The method of claim 1, wherein:
   said compound provided in Step A is $K_2 Fe O_4$.

6. The method of claim 1, wherein:
   said compound provided in Step A is formed of a salt ferrate (VI) which combines with water in the blood or aqueous media to eliminate substantially all hydroxide ($OH^-$) which cause a stinging sensation.

7. The method of claim 1, wherein said aqueous media includes:
   whole blood taken directly from the wound;
   deionized water;
   aqueous sodium chloride;
   aqueous dissolved gelatin;
   aqueous carboxy methacel; and
   aqueous carbohydrate solution.

8. A method of promoting healing of a bleeding wound comprising the steps of:
   A. mixing a substantially anhydrous compound of a salt ferrate, which hydrates in the presence of water to produce $Fe^{+++}$ and oxygen, combined with an insoluble cation exchange material, with a quantity of an aqueous media to form a spreadable paste;
   B. promoting blood clotting, followed by blood flow stoppage, by applying said paste to the bleeding wound within a short working time after Step A;
   C. substantially reducing the level of bacteria, virus and fungus at the wound during Step B by the presence of said oxygen;
   D. forming a protective coating over the wound during Step B.

9. The method of claim 8, wherein:
   said compound provided in Step A is formed of a salt ferrate of H, Li, Na, K, Rb, Cs or Fr.

10. The method of claim 8, wherein:
    said salt ferrate provided in Step A is formed of a salt ferrate of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi Al, As, $NH_4$ or $N(C_4H_9)_4$.

11. The method of claim 8, wherein:
    said salt ferrate provided in Step A is formed of a salt ferrate of H, Li, Be, Na, Mg, K, Ca, Rb, Sr, Cs, Ba, Fr, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, Tl, Pb, Bi Al, As, $NH_4$ or $N(C_4H_9)_4$.

12. The method of claim 8, wherein:
    said salt ferrate provided in Step A is $K_2 Fe O_4$.

13. The method of claim 8, wherein:
    said compound provided in Step A includes a salt which combines with water in the blood to eliminate substantially all hydroxide ($OH^-$) which cause a stinging sensation.

14. The method of claim 8, wherein:
    said insoluble exchange material is a cation exchange resin.

15. The method of claim 8, wherein said aqueous media includes:
    whole blood taken directly from the wound;
    deionized water;
    aqueous sodium chloride;
    aqueous dissolved gelatin;
    aqueous carboxy methacel; and
    aqueous carbohydrate solution.

16. A method of arresting the flow of blood and other body fluids containing protein from an open skin wound comprising the steps of:
    A. mixing a substantially anhydrous compound of a monovalent, divalent or a trivalent salt ferrate which hydrates in the presence of blood to produce $Fe^{+++}$, thereby promoting clotting of the blood, with a quantity of an aqueous media to form a paste;
    B. applying said paste to the wound within a short working time of said paste of about five minutes and for a time sufficient to effect sufficient clotting of the blood to arrest substantial further blood or body fluid flow from the wound.

17. The method of claim 16, wherein said aqueous media includes:
    whole blood taken directly from the wound;
    deionized water;
    aqueous sodium chloride;
    aqueous dissolved gelatin;
    aqueous carboxy methacel; and
    aqueous carbohydrate solution.

18. A method of providing a spreadable paste and promoting healing of an open surface wound from which blood or other body fluids with protein are flowing, comprising the steps of:
    A. mixing a substantially anhydrous compound of a monovalent, divalent, or a trivalent salt ferrate, which hydrates in the presence of water to produce $Fe^{+++}$ and oxygen, with an insoluble cation exchange material in granular or powder form and combining the mixture of said salt ferrate and insoluble cation exchange material with a quantity of an aqueous media to form a spreadable paste;
    B. promoting blood and other body fluid clotting, followed by flow stoppage, by applying said paste to the open wound;
    C. substantially reducing the level of bacteria, virus and fungus at the wound during Step B by the presence of said oxygen;

D. forming a protective coating over the wound during Step B.

19. The method of claim 18, wherein said aqueous media includes:
   whole blood taken directly from the wound;
   deionized water;
   aqueous sodium chloride;
   aqueous dissolved gelatin;
   aqueous carboxy methacel; and
   aqueous carbohydrate solution.

* * * * *